(12) United States Patent
Dhepe et al.

(10) Patent No.: US 9,051,244 B2
(45) Date of Patent: Jun. 9, 2015

(54) DEPOLYMERIZATION OF LIGNIN USING SOLID ACID CATALYSTS

(75) Inventors: Paresh Laxmikant Dhepe, Maharashtra (IN); Deepa Ayillath Kutteri, Maharashtra (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 296 days.

(21) Appl. No.: 13/467,128

(22) Filed: May 9, 2012

(65) Prior Publication Data

US 2012/0302796 A1    Nov. 29, 2012

Related U.S. Application Data

(63) Continuation-in-part of application No. 13/500,131, filed as application No. PCT/IN2010/000047 on Jan. 27, 2010.

(51) Int. Cl.
| | |
|---|---|
| C07C 37/54 | (2006.01) |
| C07C 37/00 | (2006.01) |
| C07C 41/01 | (2006.01) |
| C07C 45/42 | (2006.01) |
| C07C 51/093 | (2006.01) |

(52) U.S. Cl.
CPC .............. *C07C 37/004* (2013.01); *C07C 41/01* (2013.01); *C07C 45/42* (2013.01); *C07C 51/093* (2013.01)

(58) Field of Classification Search
None
See application file for complete search history.

(56) References Cited

U.S. PATENT DOCUMENTS

| | | | | |
|---|---|---|---|---|
| 5,344,921 | A | * | 9/1994 | Sudo et al. .................... 530/502 |
| 5,959,167 | A | | 9/1999 | Shabatai et al. |
| 6,100,385 | A | * | 8/2000 | Naae et al. .................... 530/502 |
| 6,172,272 | B1 | | 1/2001 | Shabatai et al. |
| 6,214,976 | B1 | | 4/2001 | Watanabe et al. |
| 7,084,293 | B2 | * | 8/2006 | Rosier et al. .................. 558/335 |
| 2008/0050792 | A1 | | 2/2008 | Zmierczak et al. |
| 2009/0118494 | A1 | * | 5/2009 | Blair et al. .................... 536/127 |
| 2010/0137663 | A1 | | 6/2010 | Chen et al. |
| 2010/0137665 | A1 | | 6/2010 | Chen |

FOREIGN PATENT DOCUMENTS

| | | |
|---|---|---|
| JP | 2006-129735 A | 5/2006 |
| WO | 96/40970 A1 | 12/1996 |
| WO | 2009/021733 | 2/2009 |

OTHER PUBLICATIONS

Machine English Translation of 2006-129735 A published May 25, 2006.

* cited by examiner

*Primary Examiner* — Melvin C Mayes
*Assistant Examiner* — Stefanie Cohen
(74) *Attorney, Agent, or Firm* — Ladas & Parry LLP (57) ABSTRACT

The invention provides for a process for the depolymerization of lignin in an inert atmosphere to result in substituted phenolic monomer compounds. The process is catalyzed by heterogeneous solid acid catalysts and is carried out in batch or continuous mode.

10 Claims, 3 Drawing Sheets

DEPOLYMERIZATION OF LIGNIN USING SOLID ACID CATALYSTS

CROSS-REFERENCES TO RELATED APPLICATIONS

The present application is a continuation-in-part of U.S. patent application Ser. No. 13/500,131 filed Apr. 4, 2012, which is a 371 of International Application PCT/IN2010/000047 filed 27 Jan. 2010 entitled "A One Pot And Single Step Hydrolytic Process For The Conversion Of Lignocellulose Into Value Added Chemicals", which was published in the English language on 4 Aug. 2011, with International Publication Number WO 2011/092711 A1, the content of which is incorporated herein by reference.

FIELD OF THE INVENTION

The present invention relates to an improved process for depolymerization of lignin using solid acid catalyst in the absence of hydrogen and in an inert atmosphere to yield substituted phenolic monomer compounds.

BACKGROUND AND PRIOR ART OF THE INVENTION

Lignin is a complex chemical compound most commonly derived from wood and one of the most abundant organic polymers on Earth. Lignin is typically deposited in nearly all vascular plants and provides rigidity and strength to their cell walls. As a biopolymer, lignin is unusual because of its heterogeneity and lack of a defined primary structure.

Lignin refers to a biomass material which is a cross-linked racemic macromolecule with molecular masses in excess of 10,000 u. It is relatively hydrophobic and aromatic in nature. The degree of polymerisation in nature is difficult to measure, since it is fragmented during extraction and the molecule consists of various types of substructures which appear to repeat in a haphazard manner.

The lignin polymeric structure is composed primarily of three phenylpropanoid building units: p-hydroxyphenylpropane, guaiacylpropane, and syringylpropane interconnected by etheric and carbon-to-carbon linkages. Generally, in unprocessed lignins, two thirds or more of these linkages are ether bonds, while the remaining linkages are carbon-carbon bonds. Different types of lignin differ significantly in the ratio between these monomers.

Numerous efforts on lignin conversion to high-value fuels and fuel additives have included a number of single stage processing methods including hydrocracking, cracking, hydrogenation, hydrotreating, liquefaction in hydrogen-donor solvents, and the like. However, to date, these approaches have achieved limited success for a variety of reasons. During the past few years several studies have been initiated to develop two-stage processes for making liquid fuels and fuel additives from lignin.

Further, there is ample literature available on depolymerization of lignin. The vast majority of lignin research in terms of transportation fuel production is done that utilize gaseous hydrogen and different catalysts to remove the covalently bound oxygen as water.

References may be made to U.S. Pat. No. 6,214,976, wherein inventor discloses a process for depolymerizing and/or chemically modifying lignin or lignin-like compounds using a solution of copper and peroxide at a temperature of less than 100° C.

References may be made to U.S. Pat. No. 5,959,167, wherein inventor describes a process for converting lignin into reformulated hydrocarbon gasoline, comprising subjecting the lignin material to a base-catalyzed depolymerization to produce a depolymerized lignin product consisting of alkylated phenols, alkylated alkoxyphenols, hydrocarbons, and mixtures thereof; Further, the depolymerized lignin product is subjected to a sequential two-step hydroprocessing reaction (HPR) to produce a reformulated hydrocarbon gasoline product.

References may be made to U.S. Pat. No. 6,172,272, wherein inventor discloses a process for converting lignin into reformulated partially oxygenated gasoline comprising subjecting the lignin material to a base-catalyzed depolymerization reaction in the presence of a supercritical alcohol at 240° C.-270° C.; followed by selective hydrocracking reaction at 340° C.-375° C., which utilizes superacid catalyst (platinum-modified catalyst) to produce a high oxygen-content depolymerized lignin product mainly composed of alkylated phenols, alkylated alkoxyphenols, and alkylbenzenes. In the second stage of the process, the depolymerized lignin product is subjected to an exhaustive etherification reaction with MeOH in presence of a catalyst; optionally followed by a partial ring hydrogenation reaction to produce a reformulated, partially oxygenated/etherified gasoline product, which includes a mixture of substituted phenyl/methyl ethers, cycloalkyl methyl ethers, C7-C10 alkylbenzenes, C6-C10 branched and multibranched paraffins, and alkylated and polyalkylated cycloalkanes.

References may be made to U.S. Pat. No. 6,100,385, wherein inventor discloses a method of producing lignin phenol from lignin, which comprises placing lignin in contact with a hydrogen donor organic solvent such as tetralin, lignin phenol or biomass oil; converting the lignin into low molecular weight-lignin phenol by reducing the lignin in the presence of a reducing agent (such as CO, H2, H2S and mixture thereof) and a catalyst at a temperature preferably about 300° C. to about 550° C., wherein said catalyst contains molybdenum oxide and a second component selected from the group consisting of nickel oxide or cobalt oxide supported on alumina (neutral, acidic or basic).

References may be made to US2008050792, wherein inventor discloses a process for conversion of a lignin material to a bio-fuel, comprising subjecting the lignin material to a base catalyzed depolymerization reaction at a temperature of 230° C.-350° C. to produce a partially depolymerized lignin, which is a mixture of monomeric and oligomeric alkylated phenols, biphenols, alkoxyphenols and some hydrocarbons; subjecting the partially depolymerized lignin to a stabilization/partial hydrodeoxygenation reaction in the presence of a solid metal catalyst containing one or more metals selected from the group consisting of Group VI and Group VIII metals of the Periodic Table and vanadium and combinations thereof on a solid support at a temperature of about 200° C. to 300° C. to form a partially hydrodeoxygenated product; followed by hydroprocessing step to yield bio fuel.

References may be made to WO2009021733, wherein inventor discloses a method of converting a lignin material into a liquid product, wherein lignin material is subjected to a treatment in a reaction medium of at least one C1-C2 carboxylic acid, and/or salts and/or esters thereof; optionally at least one alcohol and/or water; optionally an alkylating agent, and optionally an inorganic salt under elevated pressure to yield a liquid product. The said method is carried out in the absence of added gaseous $H_2$ and/or in the absence of any added catalyst at reaction temperature from 320° C.-420° C.

References may be made to US2010137663, wherein inventor relates to a process for producing chemicals from lignin comprising: combining lignin with a hydrogenation catalyst under hydrogen atmosphere along with base selected from the group consisting of alkali metal hydroxides, alkaline earth metal hydroxides, alkaline earth metal oxides, alkali metal carbonates, and mixtures thereof; reacting the mixture in lignin hydrolysis process conditions at a temperature between 250° C. and 450° C. to form an intermediate product stream having a reduced oxygen content; and contacting the intermediate product stream with a deoxygenation and a dehydrogenation catalyst at dehydrogenation reaction conditions including a temperature of between 400° C. and 900° C. thereby generating a product stream comprising aromatic compounds.

These methods are not environmentally benign and are energy consuming. Hence, it is required to develop a process which will not use soluble base, will operate at milder reaction conditions, and will be environmentally benign.

References may be made to US2010137665, wherein inventor discloses a process for the production of hydrocarbons and hydrogen from lignin wherein the first step comprises combining lignin with water and an acidic or basic catalyst in the presence or absence of hydrogen atmosphere to form a mixture of hydrocarbons and light oxygenates with some undecomposed lignin. For acidic depolymerization, it is preferred to have a hydrogen atmosphere. The second step involves decomposing light oxygenates to hydrogen and carbon dioxide in presence of a decomposition catalyst to form a second intermediate stream comprising hydrogen; followed by a third step of combining second intermediate stream with a hydrogenation catalyst to form decomposed lignin, hydrogenated or partially hydrogenated compounds; further contacting the third stream with a dehydrogenation catalyst to form a stream comprising aromatic compounds. It is a process to produce hydrocarbons from lignin, without the addition of an external source of hydrogen, the process itself generates hydrogen that is used in the process.

However, there is still a need in the art for an improved and environment friendly process for depolymerization of lignin which will ameliorate the drawbacks of existing prior processes.

OBJECTIVE OF THE INVENTION

Main objective of the present invention is to provide an improved process for depolymerization of lignin using solid acid catalyst.

Another objective of the invention is to carried out the depolymerization process in the absence of hydrogen and in an inert atmosphere to yield substituted phenolic monomer compounds.

SUMMARY OF THE INVENTION

Accordingly, present invention provides an one pot and single step process for the conversion of lignin to substituted phenolic compounds using heterogeneous solid acid catalyst and the said process comprising the steps of:
  i. charging lignin and catalyst in the ratio ranging between 0.1:1 to 1:0.1 in a reactor followed by charging a solvent;
  ii. optionally flushing the reactor with inert gas or air;
  iii. adjusting the pressure to 1 to 70 bar and temperature in the range of 50 to 300° C. of the reactor, under stirring;
  iv. raising the stirring speed to 10 to 2000 rpm after stabilizing the required temperature;
  v. carrying the above said reaction for period in the range of 0.1 to 96 hrs to obtain substituted phenolic compounds.

In an embodiment of the present invention, heterogeneous solid acid catalyst used is selected from the group consisting of zeolite, clays, metal oxides, mixed metal oxides, supported metal oxides, acid treated oxides.

In another embodiment of the present invention, inert gas used in step (b) is selected from the group consisting of nitrogen, argon, helium and hydrogen.

In yet another embodiment of the present invention, solvent used is selected from the group consisting of organic solvent or a mixture of water and organic solvent in a ratio of 1:99 to 99:1 and said organic solvent is selected from the group consisting of alcohols, esters, hexane, acids, toluene and xylene.

In yet another embodiment of the present invention, said catalyst is recyclable and reusable.

In yet another embodiment of the present invention, substituted phenolic monomer compounds are represented by general formula 1 wherein,
R1=—H, —OH, —OCH₃, —OCH₂—CH₃, —CH=CH₂, —CH=CH—CH₃,
R2=—H, —OH, —OCH₃, —OCH₂—CH₃, —CH=CH₂, —CH=CH—CH₃, —CO—CH₃, —CO—CH=CH₂, —CH₂—CH₃, —CH₂—CH₂—CH₃, —CHO, —CHOH—CHOH—CH₃, —CHOH—CO—CH₂OH, —C(CH₃)₃;
R3=—H, —OH, —OCH₃, —OCH₂—CH₃, —CH=CH₂, —CH=CH—CH₃, —CO—CH₃, —CO—CH=CH₂, —CH₂—CH₃, —CH₂—CH₂—CH₃, —CHO, —CH₂—CO—CH₃, —CH₂OH, —CH₂—CH₂OH, —CO—OCH₃, —CH₂—COOH, —CH=CH—CHO, —CH=CH—COOH, —CH₂—CH₂—CH₂—CH₃, -Ph/Ar, —O-Ph/Ar;
R4=—H, —OH, —OCH₃, —OCH₂—CH₃, —CH=CH₂, —CH=CH—CH₃, —CO—CH₃, —CH₂—CH₃, —CHO, CH₂—CH₂—CH₃, —CH₂—CH₂OH, —CH₂OH, —CH=CH—OH, —CH=CH—CH₂OH, CH₂—CO—CH₃, —COOH, —CH₂—COOH, —CH=CH—CHO, —CH=CH—COOH, —CH₂—CH₂—CH₂—CH₃, —OCH₂R1, -Ph/Ar, —O-Ph/Ar.

In yet another embodiment of the present invention, said process is conducted in batch mode.

In yet another embodiment of the present invention, said process is conducted in continuous mode.

In yet another embodiment of the present invention, products are soluble in any of the following category of solvents in pure form or in mixture (with varying ratios) of thereof such as Polar, non-polar, polar protic, polar aprotic, aromatics, substituted aromatics, hydrocarbons, halogenated, aldehydes, ketones, alcohols, ethers, acetates, volatiles and non-volatiles.

In yet another embodiment of the present invention, depending up on the reaction conditions employed after the reaction and evaporating reaction media, final mass may be obtained as solid or as viscous oil.

In yet another embodiment of the present invention, products may have molecular weight in the range of 100-400 having varying substituent groups.

BRIEF DESCRIPTION OF THE DRAWING

m/z values for q to a' compounds are q) (m/z=220,192,178,167) z) (m/z=341,295,281,221)
r) (m/z=220,149,131,73) a') (m/z=202,188,179,173,160,149)
s) (m/z=272,256,243,226,212,198,187)
t) (m/z=280,237,223,149)
u) (m/z=330,262,177,164)
w) (m/z=281,264,234,222)
x) (m/z=296,281,236,221,180)
y (m/z=298,255,241,213,199)

DETAILED DESCRIPTION OF THE INVENTION

P-coumaryl alcohol

Conifreyl alcohol

-continued

Sinapyl alcohol

Lignin is one of the main constituent among the 3 major constituents of the lignocellulosic biomass. The other two constituents are cellulose and hemicelluloses. The main role of lignin in plant cell walls is to stick together cellulose and hemicellulose. Normally, 10-30 wt % (dry) of lignin is present in lignocellulosic biomass. Lignin is a 3-D amorphous polymer made up of several units of aromatic compounds joined together. The aromatic rings may have varying substituent groups such as hydroxyl, alkoxy, ether, alkyl, aldehyde, ketone, etc. The composition, and molecular weight of lignin differ from plant to plant. The percentage of lignin in the cell wall varies with the type of plant whether it is a tree, bush, hurb, grasses etc. The 3 major building blocks of lignin are as follows.

The molecular weight of lignin generally ranges from 300 to 20,000. However, it is also possible to have lignins with higher molecular weights such as, 70,000 and more. There are several kind of linkages in lignin like β-O-4, β-5, 5-5, 4-O-5 etc. which depicts C—C and C—O linkages, among them β-O-4 linkage is dominant, consisting of more than half of the linkage structures of lignin. Following is a typical structure of lignin, though confirm structure of lignin is yet to be derived.

It is possible to isolate the lignin from other constituents such as cellulose and hemicellulose by various pre-treatment or isolation techniques. Depending on the technique by which lignin is isolated the names for lignin are given. For e.g. if lignin is extracted using organic solvent (solvent extraction) then it is called as, Organosolv. If lignin is extracted using alkali treatment then it is called as, Kraft or alkaline lignin. There are many other types of lignin such as, Klason Willstaetter, Pyrolytic, dealkaline lignin etc.

Present invention provides an improved process of depolymerization of lignin using solid acid catalyst in the absence of hydrogen and in an inert atmosphere to yield substituted phenolic monomer compounds and gases (CO, $H_2$, $CH_4$, alkanes etc.).

The catalyst used in the depolymerization reaction is selected from zeolite, clays, metal oxides, acid treated oxides etc. These catalysts work at milder reaction conditions and are also easy to separate from reaction mixture and are recyclable. The reaction is carried out at a temperature below 300° C., preferably in the temperature range of 215° C. to 300° C.

The catalyst used in the depolymerization reaction is selected from zeolite, clays, metal oxides, acid treated oxides etc. These catalysts work at milder reaction conditions below 270° C. and the said reaction resulted into 65% yield with almost more than 85% mass balance.

Lignin derived from organosolv process, solid acid catalyst, mixture of water and organic solvent are charged in an autoclave. According to the invention, ratio of organic solvent to water varies between 0.15:0.85 to 0.85:0.15. The organic solvent is selected from alcohols, ethers, esters, acids, aldehydes, ketones, halogenated and non-halogenated having different polarities and dielectric constants, alone or in combinations thereof, preferably, Toluene, methanol, ethanol, phenol and water preferably water.

The reaction is typically carried out in the temperature range of 215° C. to 300° C. for a time period of 5 minutes to 2 hours.

Lignin, HUSY (Si/Al=15) and mixture of water and organic solvent (30 g) were charged in an autoclave (batch reactor). After flushing the reactor with nitrogen gas, nitrogen of at least 2 bar was charged. Reactor was heated up to 230° C. under the stirring (100 rpm). After attaining the desired temperature of 230° C. stirring was increased up to 500 rpm. Reaction was stopped after 30 minutes. Analysis of reaction mixture was done by GC, GC-MS.

Solid catalyst having acid functionality of the present invention depolymerizes lignin into phenolic compounds with >25% yield with almost more than 85% mass balance. High mass balance obtained in the process is due to low loss in the form of gas. The earlier known processes end up with low mass balance due to degradation of products or formation of gaseous products. From the GC-MS analysis it is found that the phenolic compounds (m/z ranges from 124 to 220) are obtained and accordingly probable structures are derived which are in accordance with the reported structures obtained under different reaction systems.

Figure 3:
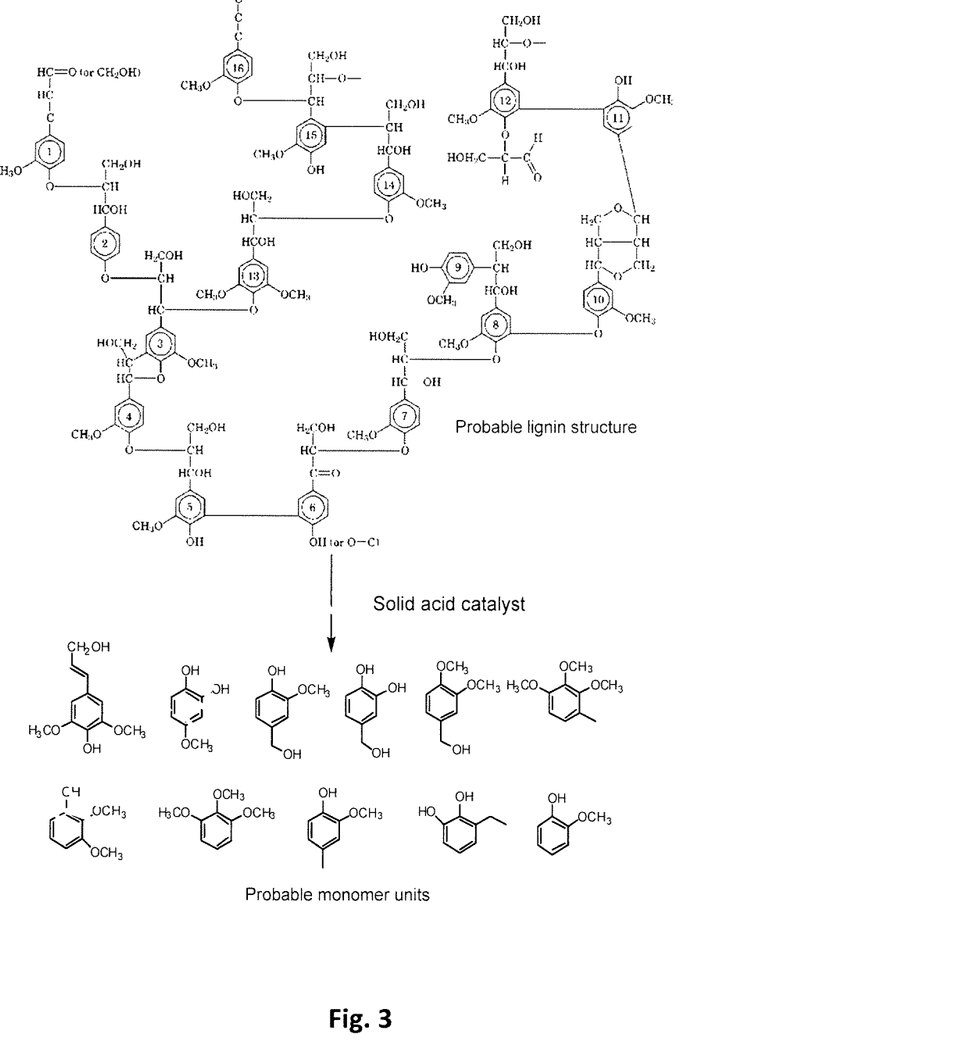
FIG. 3 represents depolymerization of lignin (a component of lignocellulosic material) using solid acid catalysts.

Depolymerization of lignin (a component of lignocellulosic material) using solid acid catalysts is shown in FIG. 3.

Phenolic compounds derived from the process of the invention comprise compound of general formula I wherein,
R1=—H, —OH, —OCH$_3$, —OCH$_2$—CH$_3$, —CH═CH$_2$, —CH═CH—CH$_3$
R2=—H, —OH, —OCH$_3$, —OCH$_2$—CH$_3$, —CH═CH$_2$, —CH═CH—CH$_3$, —CO—CH$_3$, —CO—CH═CH$_2$, —CH$_2$—CH$_3$, —CH$_2$—CH$_2$—CH$_3$, —CHO, —CHOH—CHOH—CH$_3$, —CHOH—CO—CH$_2$OH, —C(CH$_3$)$_3$.
R3=—H, —OH, —OCH$_3$, —OCH$_2$—CH$_3$, —CH═CH$_2$, —CH═CH—CH$_3$, —CO—CH$_3$, —CO—CH═CH$_2$, —CH$_2$—CH$_3$, —CH$_2$—CH$_2$—CH$_3$, —CHO, —CH$_2$—CO—CH$_3$, —CH$_2$OH, —CH$_2$—CH$_2$OH, —CO—OCH$_3$—CH$_2$—COOH, —CH═CH—CHO, —CH═CH—COOH, —CH$_2$—CH$_2$—CH$_2$—CH$_3$, -Ph/Ar, —O-Ph/Ar.
R4=—H, —OH, —OCH$_3$, —OCH$_2$—CH$_3$, —CH═CH$_2$, —CH═CH—CH$_3$, —CO—CH$_3$, —CH$_2$—CH$_3$, —CHO, CH$_2$—CH$_2$—CH$_3$, —CH$_2$—CH$_2$OH, —CH$_2$OH, —CH═CH—OH, —CH═CH—CH$_2$OH, CH$_2$—CO—CH$_3$, —COOH, —CH$_2$—COOH, —CH═CH—CHO, —CH═CH—COOH, —CH$_2$—CH$_2$—CH$_2$—CH$_3$, —OCH$_2$R1, -Ph/Ar, —O-Ph/Ar.

Figure 1:
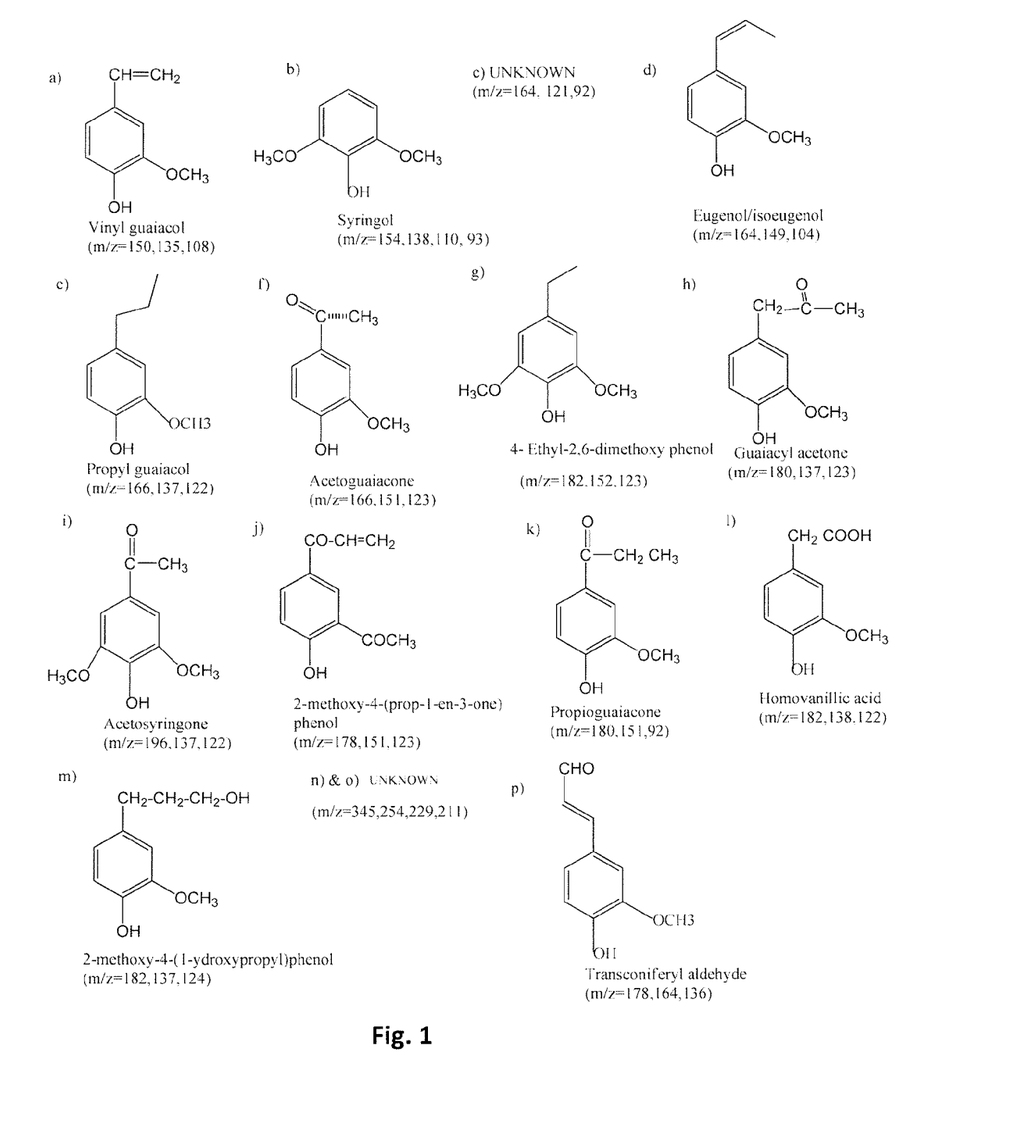
FIG. 1 depicts the monomer compounds (a to p) derived by the process according to the present invention.
Figure 2:
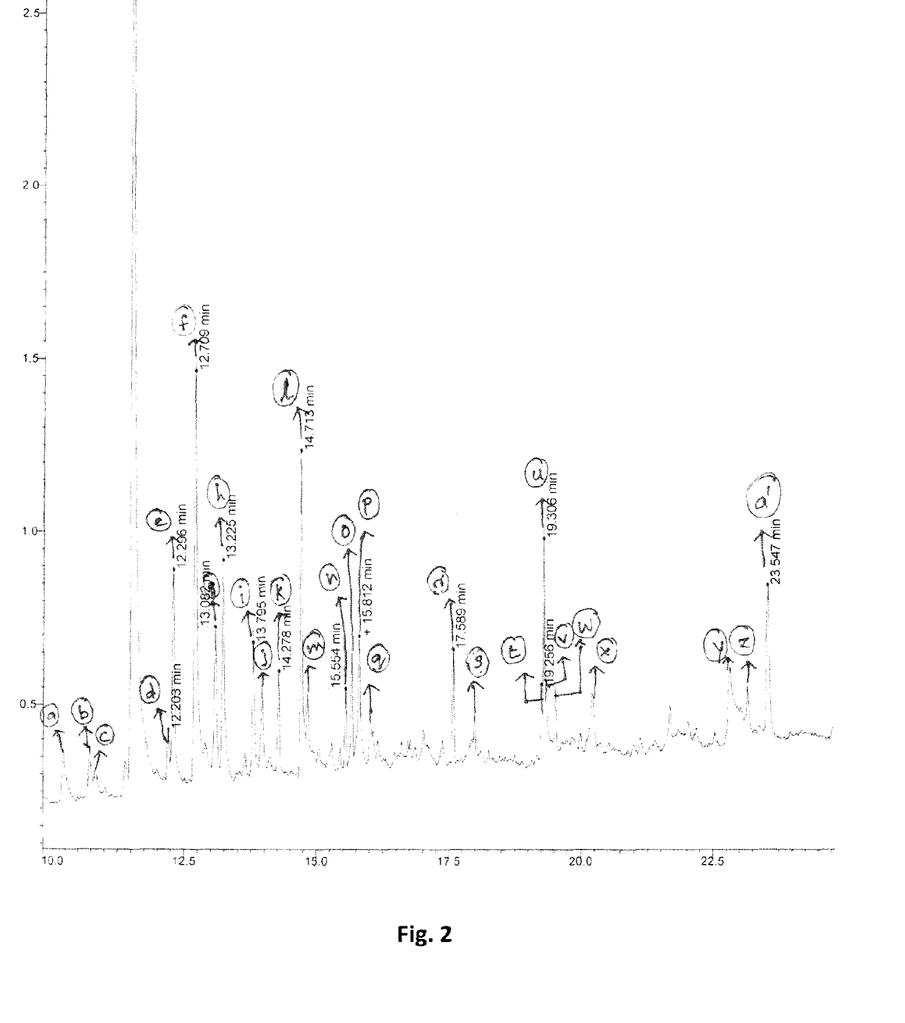
FIG. 2 represents the GCMS of phenolic compounds (a to p and q to a') of general formula 1.

The alkyl chains, aldehydes, acids, hydroxyl groups are attached to ring or to substituent's in different combinations. The preferred embodiments of the phenolic products by the process of the invention are as depicted in FIG. 1.

The process of the invention is carried out in batch mode.

The process is carried out in continuous mode in fixed bed reactor. The lignin solubilised in water or organic solvents from the group of alcohols, ethers, esters, acids, aldehydes, ketones, halogenated and non-halogenated having different polarities and dielectric constants is used as a feed. The solvents used can be in the pure form or mixture of different solvents with changing ratio. The concentration of feed may be from 0.5 to 50%. The catalyst can be loaded in any of the form like powder, beads, pellets, meshed particles, extrudates etc. either in the pure form or mixed with inert material. The contact time of the feed can be varied from 0.1 second to few minutes (<10 min). The temperatures used in this study can be >50° C. and <500° C. The reactions can be carried out either at atmosphere pressure or in the pressure range of 1-200 bar. The analysis of the reaction mixture can be done either online or offline.

Phenolic compounds obtained after lignin depolymerization could be used as such or as a starting material to synthesize other chemicals or can be further converted into chemicals which can be used as a fuel additive.

Further, the knowledge of conversion of hemicellulose and cellulose using solid catalysts already available, addition of knowledge on lignin depolymerization is beneficial in developing a process wherein total lignocellulosic materials (cellulose, hemicellulose and lignin) could be converted into chemicals.

EXAMPLES

The following examples are given by way of illustration therefore should not construed to limit the scope of the invention.

Example 1

General Example

In an autoclave (batch reactor) lignin (0.5 g), HUSY (Si/Al=15) (0.5 g) and mixture of water and organic solvent (30 g) were charged. After flushing the reactor with nitrogen gas for 3 times, nitrogen (7 bar) was charged. Reactor was heated up to 230° C. under the stirring (100 rpm). After attaining the desired temperature of 230° C. stirring was increased up to 500 rpm. Reaction was stopped after 30 minutes. Analysis of reaction mixture was done by GC, GC-MS. The lignin used in these examples were organosolv or dealkaline.

Yield: >25%

Mass balance: >90%.

Example 2

Effect of Temperature and Reaction Time on Depolymerization Reaction

Catalyst HUSY (Si/Al=15) as described in Example 1 was employed for lignin depolymerization reaction. The effect of reaction temperature and reaction time on depolymerization reaction is demonstrated by the results presented in Table 1.

TABLE 1

Results on depolymerization of lignin

| Expt. No. | Catalyst | Temp, ° C. | Time, min | Lignin conv., % | Product yield, % | Mass balance, % |
|---|---|---|---|---|---|---|
| 1 | HUSY (Si/Al = 15) | 215 | 30 | 22 | 24 | 95 |
| 2 | HUSY (Si/Al = 15) | 230 | 30 | 35 | 25 | 94 |
| 3 | — | 230 | 30 | 21 | 8 | 86 |
| 4 | HUSY (Si/Al = 15) | 230 | 70 | 43 | 31 | 94 |
| 5 | HUSY (Si/Al = 15) | 250 | 30 | 34 | 35 | 95 |
| 6 | — | 250 | 30 | 22 | 10 | 85 |
| 7 | HUSY (Si/Al = 15) | 250 | 70 | 47 | 27 | 89 |

Lignin, 0.5 g;
HUSY (Si/Al = 15), 0.5 g;
MeOH + $H_2O$ = 25 + 5 (wt basis);
$N_2$, 7 bar@ 25° C.

Example 3

Effect of Catalyst on Depolymerization of Lignin

Table 2 represents different catalysts used in the depolymerization reaction according to the invention. The reaction temperature and time of reaction was same, 250° C. and 70 minutes respectively, for all experiments carried out.

TABLE 2

Effect of Catalyst on depolymerization of lignin

| Expt. No. | Catalyst | Lignin conv., % | Product yield, % | Mass balance, % |
|---|---|---|---|---|
| 1 | HUSY (Si/Al = 15) | 47 | 27 | 89 |
| 2 | Clay, K10 | 40 | 16 | 88 |
| 3 | $SO_4/ZrO_2$ | 52 | 22 | 85 |
| 4 | $Nb_2O_5$ | 38 | 23 | 93 |

Lignin, 0.5 g; Catalyst, 0.5 g; MeOH + $H_2O$ = 25 + 5 (wt basis); $N_2$ pressure, 7 bar@ 25° C.

Example 4

Effect of Pressure on Depolymerization of Lignin

Catalyst HUSY (Si/Al=15) as described in Example 1 was employed for lignin depolymerization reaction for 30 minutes to see the effect of pressure on depolymerization reaction of lignin. Results observed are presented in Table 3.

TABLE 3

Effect of pressure on depolymerization of lignin

| Expt. No. | Pressure, bar | Lignin conv., % | Product yield, % | Mass balance, % |
|---|---|---|---|---|
| 1 | 7 | 30 | 22 | 96 |
| 2 | 1 | 44 | 37 | 96 |

Lignin, 0.5 g; HUSY (Si/Al = 15), 0.5 g; MeOH + $H_2O$ = 15 + 15 (wt basis); Temperature, 250° C.

Example 5

Effect of Different Gases on Depolymerization of Lignin

Table 4 represents the results of experiments carried out employing different gases such as $N_2$ and $H_2$ in the lignin depolymerization reaction for 70 minutes employing HUSY (Si/Al=15) as catalyst.

TABLE 4

Effect of different gases on depolymerization of lignin

| Expt. No. | Pressure, bar | Lignin conv., % | Product yield, % | Mass balance, % |
|---|---|---|---|---|
| 1 | $N_2$, 7 | 47 | 27 | 90 |
| 2 | $H_2$, 7 | 52 | 17 | 82 |

Lignin, 0.5 g; HUSY (Si/Al = 15), 0.5 g; MeOH + $H_2O$ = 25 + 5 (wt basis); Temperature, 250° C.

Example 6

Effect of Different Solvent Ratio on Depolymerization of Lignin

The Catalyst HUSY (Si/Al=15) as described in Example 1 with varying solvent ratios of the same solvent was employed in depolymerization reaction of lignin for 30 minutes. Results of the experiments are represented in Table 5.

TABLE 5

Effect of solvent ratio on depolymerization of lignin

| Expt. No. | MeOH + $H_2O$ (wt + wt) | Lignin conv., % | Product yield, % | Mass balance, % |
|---|---|---|---|---|
| 1 | 25 + 5 | 34 | 35 | 96 |
| 2 | 15 + 15 | 30 | 32 | 96 |
| 3 | 5 + 25 | Sticky mass was observed | | |

Lignin, 0.5 g; HUSY (Si/Al = 15), 0.5 g; $N_2$ Pressure, 7 bar @RT; Temperature, 250° C.

Example 7

Effect of Different Solvents on Depolymerization of Lignin

Table 6 represents different experiments carried out in presence of different solvents in the lignin depolymerization reaction according to the invention, employing HUSY (Si/Al=15) as catalyst.

TABLE 6

Effect of different solvents on depolymerization of lignin

| Expt. No. | Solvent Wt basis | Time, min | Lignin conv., % | Product yield, % | Mass balance, % |
|---|---|---|---|---|---|
| 1 | MeOH + H2O = 25 + 5 | 30 | 34 | 35 | 91 |
| 2 | Phenol + H2O = 7 + 30 | | Shows products forming. | | |
| 3 | H2O (100%) | | Shows products forming. | | |
| 4 | EtOH + H2O = 25 + 5 | 30 | 25 | 20 | 85 |
| 5 | Toluene | 30 | 23 | 10 | 87 |

Lignin, 0.5 g; HUSY (Si/Al = 15), 0.5 g; N2 Pressure, 7 bar @RT; Temperature, 250° C.

Example 8

The Effect of Catalyst on Depolymerization of Dealkaline Lignin

Table 7 represents different experiments carried out in presence of different catalyst in the lignin (dealkaline)* depolymerization reaction

| Exp. No | Catalyst | Lignin conversion, % | Product yield, %# | Mass balance, % |
|---|---|---|---|---|
| 1. | HZSM-5 | 84 | 50 | 91 |
| 2. | $SiO_2$—$Al_2O_3$ | 85 | 26 | 81 |
| 3. | $MoO_3/SiO_2$ | 90 | 28 | 91 |
| 4. | $Ga_2O_3/SiO_2$ | 45 | 15 | 92 |
| 5. | $WO_3/SiO_2$ | 90 | 55 | 85 |
| 6. | $SO_4/ZrO_2$ | 76 | 15 | 87 |
| 7. | $Nb_2O_5$ | 68 | 18 | 89 |
| 8. | K10 (clay) | 56 | 09 | 84 |

*Lignin, 0.5 g; HUSY (Si/Al = 15), 0.5 g; N2 Pressure, 7 bar @RT; Temperature, 250° C.
Monomer and dimer products soluble in water/organic solvents.

Example 9

The Effect of Time on Depolymerisation of Dealkaline Lignin

The effect of reaction temperature and reaction time on depolymerization reaction is demonstrated by the results presented in Table 8 using $SiO_2$—$Al_2O_3$ as catalyst*.

TABLE 8

| Expt. No. | Time (min.) | Lignin conversion % | Product yield, %# | Mass balance, % |
|---|---|---|---|---|
| 1. | 30 | 85 | 26 | 80 |
| 2. | 60 | 85 | 41 | 86 |
| 3. | 90 | 92 | 50 | 84 |
| 4. | 120 | 95 | 70 | 85 |

Lignin, 0.5 g; HUSY (Si/Al = 15), 0.5 g; N2 Pressure, 7 bar @RT; Temperature, 250° C.
Monomer and dimer products soluble in water/organic solvents.

Example 10

Catalyst Recyclability

Catalyst recyclability was tested and it has been found out that with $SiO_2$—$Al_2O_3$ catalyst in presence of methanol-water system at 250° C. and within 30 min. in first reaction 26% products yield was obtained. After reaction catalyst was recovered and used for the next reaction and under similar reaction conditions 24% products yield is observed.

ADVANTAGES OF THE INVENTION

1. The products obtained are value added products, useful as such or as a fuel additives
2. The process can be carried out in batch as well as continuous modes.
3. The heterogeneous acid catalysts used as corrosion-free.
4. The catalysts are easily separable from reaction mixture.
5. A safer process conducted in inert atmosphere.

We claim:

1. A process for the conversion of lignin to substituted phenolic compounds, said process comprising the steps of:
   i. charging lignin and a catalyst in the ratio ranging between 0.1:1 to 1:0.1 into a reactor followed by charging a solvent, wherein the catalyst consists of a heterogeneous solid acid catalyst;
   ii. optionally flushing the reactor with nitrogen, argon, helium, hydrogen or air;
   iii. adjusting the reactor to operate at atmospheric pressure and heating the reactor to a temperature in the range of 50 to 300° C. with stirring;
   iv. raising the stirring speed to 10 to 2000 rpm after stabilizing at the temperature; and
   v. carrying out a reaction for a period in the range of 0.1 to 96 hours to obtain substituted phenolic compounds.

2. The process as claimed in claim 1, wherein the heterogeneous solid acid catalyst is selected from the group consisting of zeolite, clays, metal oxides, mixed metal oxides, supported metal oxides, acid treated oxides.

3. The process as claimed in claim 1, wherein the solvent is selected from the group consisting of organic solvent or a mixture of water and organic solvent in a ratio of 1:99 to 99:1 and said organic solvent is selected from the group consisting of alcohols, esters, hexane, acids, toluene and xylene.

4. The process as claimed in claim 1, wherein said catalyst is recyclable and reusable.

5. The process as claimed in claim 1, wherein the substituted phenolic monomer compounds are represented by general formula 1 wherein,
R1=—H, —OH, —$OCH_3$, —$OCH_2$—$CH_3$, —CH=$CH_2$, —CH=CH—$CH_3$,
R2=—H, —OH, —$OCH_3$, —$OCH_2$—$CH_3$, —CH=$CH_2$, —CH=CH—$CH_3$, —CO—$CH_3$, —CO—CH=$CH_2$, —$CH_2$—$CH_3$, —$CH_2$—$CH_2$—$CH_3$, —CHO, —CHOH—CHOH—$CH_3$, —CHOH—CO—$CH_2$OH, —C($CH_3$)$_3$;
R3=—H, —OH, —$OCH_3$, —$OCH_2$—$CH_3$, —CH=$CH_2$, —CH=CH—$CH_3$, —CO—$CH_3$, —CO—CH=$CH_2$, —$CH_2$—$CH_3$, —$CH_2$—$CH_2$—$CH_3$, —CHO, —$CH_2$—CO—$CH_3$, —$CH_2$OH, —$CH_2$—$CH_2$OH, —CO—$OCH_3$—$CH_2$—COOH, —CH=CH—CHO, —CH=CH—COOH, —$CH_2$—$CH_2$—$CH_2$—$CH_3$, -Ph/Ar, —O-Ph/Ar;
R4=—H, —OH, —$OCH_3$, —$OCH_2$—$CH_3$, —CH=$CH_2$, —CH=CH—$CH_3$, —CO—$CH_3$, —$CH_2$—$CH_3$, —CHO, $CH_2$—$CH_2$—$CH_3$, —$CH_2$—$CH_2$OH, —$CH_2$OH, —CH=CH—OH, —CH=CH—$CH_2$OH, $CH_2-CO-CH_3$, —COOH, —$CH_2$—COOH, —CH=CH—CHO, —CH=CH—COOH, —$CH_2$—$CH_2$—$CH_2$—$CH_3$, —$OCH_2R1$, -Ph/Ar, —O-Ph/Ar.

6. The process as claimed in claim 1, wherein said process is conducted in batch mode.

7. The process as claimed in claim 1, wherein said process is conducted in continuous mode.

8. The process as claimed in claim 1, wherein the temperature is below 270° C.

9. The process as claimed in claim 1, further comprising the steps of:
   vi. recovering the substituted phenolic compounds; and
   vii. recovering the catalyst.

10. The process as claimed in claim 9, wherein the process consists essentially of steps (i), (iii), (iv), (v), (vi), and (vii), and optionally step (ii).

\* \* \* \* \*